United States Patent [19]

Baudet

[11] 4,336,394
[45] Jun. 22, 1982

[54] CYANO-UREAS, CYANO-THIOUREAS AND THEIR PREPARATION METHODS

[76] Inventor: Pierre J. Baudet, 15. ch. de Passoret, Geneva 1227, Switzerland

[21] Appl. No.: 217,112

[22] PCT Filed: Mar. 14, 1980

[86] PCT No.: PCT/CH80/00037
§ 371 Date: Nov. 14, 1980
§ 102(e) Date: Nov. 13, 1980

[87] PCT Pub. No.: WO80/01914
PCT Pub. Date: Sep. 18, 1980

[30] Foreign Application Priority Data

Mar. 14, 1979 [CH] Switzerland .................. 2393/79

[51] Int. Cl.$^3$ .......................................... C07D 233/54
[52] U.S. Cl. .................................................. 548/342
[58] Field of Search ........................................ 548/342

[56] References Cited

U.S. PATENT DOCUMENTS 4,192,879  3/1980  Durant et al. ................ 548/342

Primary Examiner—Henry R. Jiles
Assistant Examiner—Robert C. Whittenbaugh
Attorney, Agent, or Firm—Pennie & Edmonds

[57] ABSTRACT

The invention relates to cyano-urea and cyano-thiourea derivatives characterized by structures of formulas (a),(b),(c) and (d):

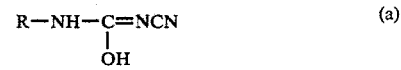

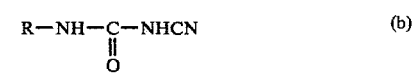

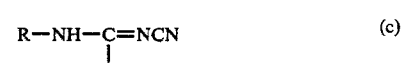

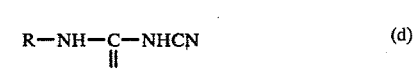

in which R is 2-mercapto-ethyl radical or 2-((4-methyl-5-imidazolyl) thiomethyl) ethyl radical. The invention relates to the manufacture of cyano-ureas and cyano-thioureas.

The compounds of invention: N-2-((4-methyl-5-imidazolyl)thiomethyl) ethyl-N'-imino-cyano-urea, N-2-((4-methyl-5-imidazolyl)thiomethyl) ethyl N'-imino-cyano-thiourea, as well as their carbonyl and thio-carbonyl tautomers are histamine antagonists in the H$_2$ receptors which inhibit the secretion of gastric acid. They can be used therapeutically for the treatment of gastric and duodenal ulcers.

3 Claims, No Drawings

CYANO-UREAS, CYANO-THIOUREAS AND THEIR PREPARATION METHODS

The cyano-urea and cyano-thiourea functional groups fixed at the end of a lateral chain of the radical 2-((4-methyl-5-imidazolyl) thiomethyl)-ethyl characterize the compound of the invention:

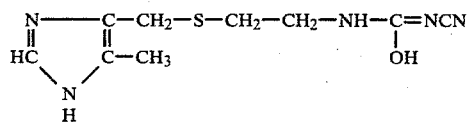
(A)

(tautomer imino-nitrile)

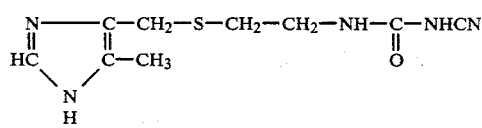
(B)

(tautomer amino-nitrile)

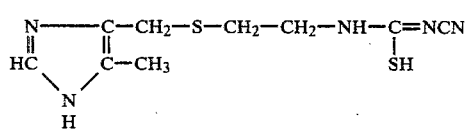
(C)

(tautomer imino-nitrile)

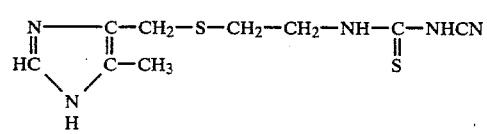
(D)

(tautomer amino-nitrile)

These functional groups determine, by their properties of acceptor and donor of hydrogen bond in the prototropic nature of their grouping and in the reciprocal interconversion of their tautomers, strong interactions with the peptidic functional groups of the polypeptides and the proteins. These interactions are schematized as per the formulas (a), (b), (c) and (d):

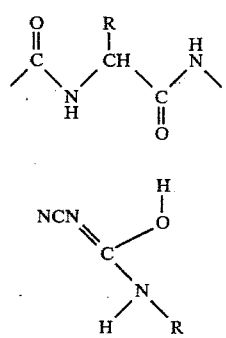
(a)

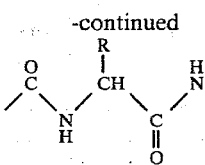
(b)

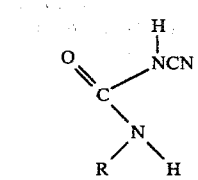

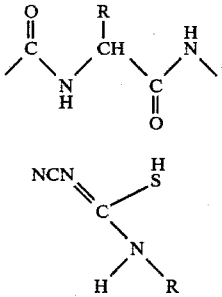
(c)

(d)

These functional groups determine by their properties of acceptor and donor of hydrogen bond strong interactions with the proteins. The hydrogen bond donated by the functional groups

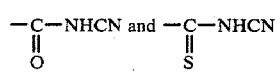

represented in the formulas (b) and (d) is particularly strong, due to the relative acidity of these functional groups that determine the electron-attraction effect of the nitrile radical on the amino-nitrogen.

The cyano-ureas and cyano-thioureas of the formulas (A), (B), (C) and (D) antagonize the histamine in the $H_2$ receptors of the gastric parietal cells. Due to this fact, these cyano-ureas and cyano-thioureas lessen or prevent the production of the hydrochloric acid by those cells.

In the $H_2$ receptors the radical imidazole of the invention's compounds is fixed in a suitable manner on a site proper to the said receptor and by which the stimulating action of histamine is being made; in other respects, the cyano-ureas and cyano-thioureas functional groups, at the other end of the molecules of the compounds of the formulas (A), (B), (C) and (D) enter into strong hydrogen bonds with another site of the same $H_2$ receptor.

These interactions allow a better fixation of the histamine's antagonist in the H₂ receptors, which lengthen the duration of the medicinal action and lessens the therapeutically useful dose.

In other respects, the cyano-urea and cyano-thiourea functional groups favor the biodisposability of the said compounds in the hydric compartment of the organism.

The invention's compounds caracterised by the formulas (A), (B), (C) and (D) can be used therapeutically for the treatment of duodenal and gastric ulcer.

The suitable excipients for the pharmaceutical preparation of the invention's compounds are, for example, lactose, saccharose, talcum, magnesium stearate, gelatine.arabic gum.olive oil.

EXAMPLE 1

N-(2-mercapro-ethyl)-N'-cyano-urea

To a solution of 5.25 g of 2-thiazolone in dry ethanol, is added 3.2 g of mono-sodium cyanamide derivative and taken to reflux 4 hours. The solvent is evaporated and the sodium-N-(2-mercapto-ethyl)N'-cyano urea is crystallized in tetrahydrofuran(IR(nujol): 3450,3350,2150,2120,1670,1610,1535,1410(sh),1305,1260,1200, 1115,1060,1040(sh),970,920,880,840,760,720 cm$^{-1}$). The crystallized fraction is dissolved in methanol, then neutralized by the equivalent quantity of HCl. The residue of evaporation is extracted with acetonitrile in order to separate NaCl. The mother liquor evaporated under reduced pressure gives the product; it is made up of a mixture of tautomers(imino-nitrile: IR 2170 and 2150 cm$^{-1}$ and amino-nitrile IR 2250 cm$^{-1}$). The imino-nitrile tautomeric fraction is not very soluble in ethyl acetate, the amino-nitrile tautomeric fraction is more soluble. IR(film) of the tautomeric mixture: 3280,2250,2170,2150,1700, 1670,1630,1550-1520,1460,1430,1390,1370,1300,1250,1230,1170, 1130,1040,1030,780-769 cm$^{-1}$.

EXAMPLE 2

N-(2-mercapto-ethyl)-N-cyano-urea 11.3 g of cysteineamine hydrochloride are dissolved in dry ethanol with 0.54 g of sodium methoxide, then 1.114 g of crystallized N-ethoxyoxy-carbonyl cyanamide is added. After 5 h. of reaction at an ordinary temperature, NaCl is isolated and one obtains a product as oil by evaporation of the solvent; which is homogeneous in c.c.m chromatography (n-butanol-acet.ac.-Water 10/2/5 vol.) revealing by sodium nitroprusside reagent (red coloring).

EXAMPLE 3

N-2-((4-methyl-5-imidazolyl)-thiomethyl)-ethyl N'-imino-cyano-urea. (tautomer imino-nitrile)

To a solution cooled in ice of 16.2 g de carbonyl di-imidazole in dry tetrahydrofuran is added drop by drop a solution in the same solvent of 17.1 g of crystallized 2-((4-methyl-5-imidazolyl)thiomethyl)-ethylamine (F.55°). After 20 minutes, a solution is added in dry ethanol of 6.4 g of the mono-sodium-cyanamide. After 3 h. of reaction, the sodium derivative of product and is crystallized in tetrahydrofuran; IR(nujol): 3390. 3100,2130,1595,1420,1340,1320,1250,1190,1060,850,820,770 cm$^{-1}$. The mono-sodium derivative is put into methanol and is neutralized under agitation with the equivalent quantity of acetic acid. From the solution the compound crystallizes as a imino-nitrile tautomer; F. 159°–161°; IR(nujol): 3200.3100, 2600,2360,2130,1640,1550,1490,1420,1320,1290(sh),1280(sh) 1260,1240,1210,1195,1050,1010,970,908,860,810,780,760,730, 705 cm$^{-1}$.

C₉H₁₃N₅SO (239) Calc. C 45,18 H 5,44 N 29,28 S 13,28% Found. C 45,24, H 5,65 N 29,23 S 13,42%

EXAMPLE 4

N-2-((4-methyl-5-imidazolyl) thiomethyl) ethyl N'-imino-cyano-urea. (tautomer imino-nitrile)

To a solution of 1.06 g of carbonyl-N-imidazole-N'-2-((4-methyl-5-imidazolyl)-thiomethyl)-ethylamine(F. 77°–80°) in acetonitrile is added a solution in dry ethanol of 0.23 g of mono-sodium-cyanamide. After 4 h. of reaction, the solvent is evaporated and the oily residue is taken with tetrahydrofuran in order to crystallize the product as a sodium derivative. From the solution in methanol, one neutralizes, with the equivalent quantity of acetic acid. The product crystallizes from this solution; F. 159°–161°. (see IR and analysis-Ex. 3

EXAMPLE 5

N-2-((4-methyl-5-imidazolyl) thiomethyl) ethyl N'-imino-cyano-urea. (tautomer imino-nitrile)

To a solution in dry ethanol cooled in ice, of 1.52 g of 2-((4-methyl-5-imidazolyl) thiomethyl) ethylamine(F. 55°), is added, in several portions and under agitation 1.80 g of carbonyl-N-imidazole-N'-cyanamide(F. 143°–145°). After 5 h. of reaction, one starts the crystallization or it occurs spontaneously; m.p. 159°–161°. (IR, see Ex. 3)

EXAMPLE 6

N-2-((4-methyl-5-imidazolyl) thiomethyl) ethyl -N'-imino-cyano-urea. (tautomer imino-nitrile)

To a solution in dry tetrahydrofuran of 2.38 g of 2-((4-methyl-5-imidazolyl) thiomethyl) ethylamine(F. 55°) is added a solution in the same solvent of 1.56 g of N-carbethoxy-cyanamide, After 2 h. of reaction, one starts the crystallization of the product, or it occurs spontaneously; m.p. 159°–161°. (IR and analysis see Ex. 3)

EXAMPLE 7

N-2-((4-methyl-5-imidazolyl) thiomethyl) ethyl-N'-imino-cyano-urea.

To a solution of 1.83 g of 4-methyl-5-chloromethyl-imidazole(as hydrochloride) in dry ethanol and under argon, is added 1.59 g of N-(2-mercapto-ethyl)-N'-cyano-urea, then 2.20 g of sodium methoxide. After 7 h. of reaction at an ordinary temperature, the last one being at reflux, NaCl is isolated; one starts the crystallisation; m.p. 159°–161°.

EXAMPLE 8

N-2-((4-methyl-5-imidazolyl) thiomethyl) ethyl -N'amino-cyano-urea(as hydrochloride). (tautomer amino-nitrile)

To a solution in methanol of 2.39 g of N-2-((4-methyl-5-imidazolyl) thiomethyl) ethyl -N-imino-cyano-urea is added an equivalent of HCl in ether. After complete dissolution, the solvent is evaporated and the hydrochloride is crystallized in acetonitrile; m.p. 140°–142°; IR(nujol): 3260(sh),3140,3050,2650, 2700(sh),2250,2150,1680,1640,1560,1485,1360(sh),1330,1310, 1245,1220,1165,1050,1020,950,920,845,700 cm$^{-1}$).

EXAMPLE 9

N,N'-carbonyle-imidazole-cyanamide(as imidazolium salt).

To a solution in dry tetrahydrofuran of 16.2 g of carbonyl di-imidazole is added drop by drop a solution of 4.2 g of cyanamide in the same solvent; a few minutes after the beginning of the addition, the product crystallizes as imidazolium salt (imino-nitrile tautomer) F. 143°–145°; perchloric titration in acetic acid, Mol weight Calc.204 found 203.7.

EXAMPLE 10

Thiazolone-2

5.67 g of cysteineamine hydrochloride is dissolved in dry ethanol and neutralized by the equivalent quantity of sodium ethoxide. After filtration, the solvent is evaporated and the obtained residue is dissolved in dry tetrahydrofuran. To this solution is added 5.05 g of triethylamine. The resulting solution is cooled in ice and under agitation drop by drop, 5.42 g of ethylchlorocarbonate is added. After 8 h. the insoluble triethylamine hydrochloride is isolated. The mother-liquor gives the product, which is crystallized in ether at $-10°$; m.p. 68 - 70°; $R_f$:0.97 t.c.c(methanol-acetic acid-ethyl acetate water, 7/1.5/2/1 vol.); IR(film): 3300,2950,2900,1710(sh), 1680,1520,1470,1450, 1440,1400,1380,1360,1300,1255,1170(sh)1140,1090,106-0,1045, 11010(sh), 780 cm$^{-1}$.

EXAMPLE 11

N,N'-carbonyle-imidazole-2-(4-methyl-5-imidazolyl)-thiomethylethylamine.

To a solution in dry tetrahydroturan of 162 f of carbonyl di-imidazole is added drop by drop a solution in the same solvent of 1.71 g of z ((4-methyl-5-imidazolyl)-thiomethyl)-ethylamine(m.p.55° ). From this solution the product of the reaction is crystallized ; mp. 77–80° ; IR(nujol): 3100,1700,1600,1540, 1400, 1380, 1360,1300,1255,1170(sh), 1140,1090,1060,1045, 10106sh), 780 cm$^{-1}$.

EXAMPLE 12

N-2-((4methyl-5-imidazolyl) thiomethyl) ethyl N-imino-cyano-thiourea (tautomer imino-nitrile)

To a cooled solution in ice, in dry tetrahydroturan of 3.28 g of thio-carbonyl di-imidiazole is added, drop by drop, a solution in the same solvent of 3.14 g of 2-((4-methyl-5-imidazoily) thiomethyl) ethylamine (m.p. 55° ). After 30 minutes reaction, a sample is taken for IR spectroscopic analysis which indicates the formation of N,N' thio-carbonyl-imidazole) thiomethyl) ethylamine and the formation of isothiocyanate of the introduced amine introduced amine (2170 and 2080 cm$^{-1}$), 117 g of mono-sodium cyanamide in suspension in dry ethanol is then introduced into the solution. After 4 h. of reaction, the product is isolated as sodium-derivative,IR(frilm): 2150.

1630,1530,1465,1420,1150,1120,1080,1060,1055,1040,95-0,910, 880,820,750 cm$^{-1}$.

The previous sodium-derivative is neutralized with an equivalent of HCl in ether, in ethanol. After filtration, the solvent is evaporated under reduced pressure. The residue is extracted with ethyl acetate; the soluble fraction gives the product as oil; IR(film): 3100,3000,2150,1630,1515(sh),1565,1420,1350, 1320,1180,1150,1220(sh),1100,1060,850,830,750 cm$^{-1}$,

EXAMPLE 13

N-2-((4-methyl-5-imidazolyl) thiomethyl) ethyl -N'-cyanothiourea(tautomer imino-nitrile).

To a solution of 314 g of 2-((4-methyl-5-imidazolyl) thiomethyl)-ethylamine in dry ethanol, is added, in several portions and under agitation, 4 g of crystallized N,N'-thio-carbonyl-imidazole-cyanamide (imidazolium salt). One neutralizes the medium with an equivalent of HCl; the solvent is evaporated, the residue extracted with ethyl acetate, of which the evaporation gives the product as oil. (IR; see EX. 12)

EXAMPLE 14

N,N'-thio-cabonyl-imidazole-cyanamide (imidazolium salt).

To a solution of 3.56 g of thio-carbonyl di-imidazole, cooped in fee, in tetrahydrofuran, is added, drop by drop, a solution in the same solvent of 0.84 g of cyanamide, From this solution, the product crystallizes ; m.p. 148°–150°.

What we claim is:

1. Cyano-ureas having the formula:

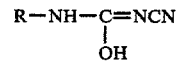

characterized by the imino-nitrile tautomer structure, wherein R is a 2-((4-methyl-5imidazolyl) methylthio ethyl radical.

2. Cyano-ureas having the formula:

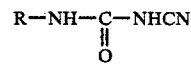

characterized by the amino-nitrile tautomer structure, wherein R is a 2-((4-methyl-5-imidazoly) myethylthio) ethyl radical.

3. Cryano-thioureas having the formula:

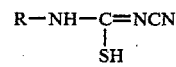

characterized by the imino-nitrile tautomer structure, wherein R is a 2-((4-methyl-5-imidazoly) methylthio) ethyl radical.

* * * * *